(12) United States Patent
Sughrue et al.

(10) Patent No.: US 11,004,462 B1
(45) Date of Patent: May 11, 2021

(54) MACHINE LEARNING CLASSIFICATIONS OF APHASIA

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/028,826

(22) Filed: Sep. 22, 2020

(51) Int. Cl.
*G10L 25/00* (2013.01)
*G10L 25/66* (2013.01)
*G16H 50/20* (2018.01)
*G16H 30/20* (2018.01)
*G16H 30/40* (2018.01)
*A61B 5/00* (2006.01)
*G10L 15/08* (2006.01)
*G10L 15/06* (2013.01)
*G10L 15/26* (2006.01)
*G16H 10/20* (2018.01)

(52) U.S. Cl.
CPC ............ *G10L 25/66* (2013.01); *A61B 5/4803* (2013.01); *A61B 5/7267* (2013.01); *G10L 15/063* (2013.01); *G10L 15/08* (2013.01); *G10L 15/26* (2013.01); *G16H 10/20* (2018.01); *G16H 30/20* (2018.01); *G16H 30/40* (2018.01); *G16H 50/20* (2018.01)

(58) Field of Classification Search
None
See application file for complete search history.

(56) References Cited

U.S. PATENT DOCUMENTS

| 9,763,617 B2 * | 9/2017 | Quatieri | G10L 15/04 |
| 9,936,914 B2 * | 4/2018 | Quatieri, Jr. | G10L 15/04 |
| 2009/0191521 A1 * | 7/2009 | Paul | G10L 17/16 434/169 |
| 2009/0208913 A1 * | 8/2009 | Xu | A61B 5/4803 434/169 |
| 2012/0209606 A1 * | 8/2012 | Gorodetsky | G10L 15/26 704/235 |
| 2013/0090927 A1 * | 4/2013 | Quatieri | G10L 25/18 704/249 |

(Continued)

OTHER PUBLICATIONS

H. Allende-Cid, J. Zamora, P. Alfaro-Faccio and M. F. Alonso-Sánchez, "A Machine Learning Approach for the Automatic Classification of Schizophrenic Discourse," in IEEE Access, vol. 7, p. 45544-45553, 2019, doi: 10.1109/ACCESS.2019.2908620. (Year: 2019).*

(Continued)

*Primary Examiner* — Edgar X Guerra-Erazo
(74) *Attorney, Agent, or Firm* — Fish & Richardson P.C.

(57) ABSTRACT

Methods, systems, and apparatus, including computer programs encoded on computer storage media, for performing aphasia assessment. One of the methods includes receiving a recording, generating a text transcript of the recording, and generating speech quantifying and comprehension scores which can be used to determine an aphasia classification. Another method includes performing an aphasia assessment on a brain image to obtain an aphasia classification.

11 Claims, 5 Drawing Sheets

(56) References Cited

U.S. PATENT DOCUMENTS

| | | | | |
|---|---|---|---|---|
| 2013/0166291 A1* | 6/2013 | Lech | ............... | G10L 17/26 |
| | | | | 704/232 |
| 2014/0186806 A1* | 7/2014 | Hallowell | ............ | A61B 3/112 |
| | | | | 434/167 |
| 2015/0112232 A1* | 4/2015 | Quatieri | ............ | A61B 5/7264 |
| | | | | 600/595 |
| 2017/0354363 A1* | 12/2017 | Quatieri | ............ | A61B 5/4803 |
| 2019/0156947 A1* | 5/2019 | Nakamura | ............ | G16H 50/20 |

OTHER PUBLICATIONS

M. Khan, B. N. Silva, S. H. Ahmed, A. Ahmad, S. Din and H. Song, "You speak, we detect: Quantitative diagnosis of anomic and Wernicke's aphasia using digital signal processing techniques," 2017 IEEE International Conference on Communications (ICC), Paris, 2017, pp. 1-6, doi: 10.1109/ICC.2017.7996967. (Year: 2017).*

S. Fazeli, M. Naghibolhosseini and F. Bahrami, "An Adaptive Neuro-Fuzzy Inference System for Diagnosis of Aphasia," 2008 2nd International Conference on Bioinformatics and Biomedical Engineering, Shanghai, 2008, pp. 535-538, doi: 10.1109/ICBBE.2008.130. (Year: 2008).*

Kohlschein et al., "A Machine Learning Based System for the Automatic Evaluation of Aphasia" 2017 IEEE 19th International Conference on e-Health Networking, Applications and Services (Healthcom), Oct. 2017, 6 pages.

\* cited by examiner

MACHINE LEARNING CLASSIFICATIONS OF APHASIA

TECHNICAL FIELD

This document describes technology that uses machine-learning classifiers for diagnostic classifications of medical conditions such as aphasias.

BACKGROUND

Aphasia is a language impairment, wherein the person affected exhibits deficits in comprehension of speech and the ability to read or write. Aphasia is a result of brain injury (e.g., stroke, traumatic brain injury (TBI), brain tumors, infections, or progressive brain degeneration).

Clinicians or other healthcare professionals testing for aphasia often administer aphasia assessment tests in order to either screen for, or identify a patient's aphasia type in order to suggest appropriate therapies.

SUMMARY

This specification is related to administering an aphasia assessment, wherein the aphasia assessment is performed by a system trained using machine learning. For example, a patient can follow a prompt on a recording device in order to provide a recording of spontaneous speech. The spontaneous speech recording is then converted to a text transcript and fed to a general classifier or a series of stacked classifiers to determine an aphasia classification. In an alternative embodiment, the spontaneous speech can be immediately converted to text using a speech to text processing system.

Described herein are methods comprising: receiving a recording of spontaneous speech from a subject; using a machine learning speech quantifying classifier to produce a speech quantifying score based at least in part on the spontaneous speech; generating comprehension feature values from the spontaneous speech; using a machine learning comprehension classifier to produce a comprehension score based at least in part on the comprehension feature values, the comprehension classifier trained using training comprehension feature values and corresponding training comprehension scores; determining an aphasia classification based on at least one of the speech quantifying score and the comprehension score; and using the aphasia classification to process at least one of the spontaneous speech and the subject.

In some embodiments, the method further comprises: generating speech quantifying feature values from the spontaneous speech and wherein using the machine learning speech quantifying classifier to produce the speech quantifying score based at least in part on the spontaneous speech comprises using the machine learning speech quantifying classifier to produce the speech quantifying score based at least in part on the speech quantifying feature values, the machine learning speech quantifying classifier trained using training speech quantifying feature values and corresponding training speech quantifying scores. In some embodiments, using a machine learning comprehension classifier to produce a comprehension score based at least in part on the comprehension feature values comprises using a machine learning comprehension classifier to produce a comprehension score based at least in part on the comprehension feature values and on the speech quantifying score. In some embodiments, the machine learning speech quantifying classifier is trained using training spontaneous speech and corresponding training speech quantifying scores. In some embodiments, the determining an aphasia classification based on at least one of the speech quantifying score and the comprehension score further comprises submitting the speech quantifying score and the comprehension score to an aphasia classifier to receive an aphasia classification, the aphasia classifier trained using training speech quantifying scores and training comprehension scores and corresponding training aphasia classifications. In some embodiments, determining an aphasia classification comprises determining a set of aphasia confidence values for different types of aphasia and then using those confidence values to select an aphasia classification. In some embodiments, the method generates comprehension feature values from the spontaneous speech and submits the comprehension feature values to a comprehension classifier to produce a comprehension score only if the speech quantifying score exceeds a threshold. In some embodiments, the method further comprises: receiving an initial recording, wherein the initial recording comprises i) a video recording of the subject or ii) an audio recording of the subject; and generating a text transcript from the initial recording. In some embodiments, the speech quantifying feature values comprise one or more of: sounds per minute; words per minute; unique words per minute; a verb list; a count of a number of verbs; a proportion of valid words that are verbs; a noun list; a count of a number of nouns; a proportion of valid words that are nouns; a count of number of times a word was repeated twice in a row; and a representation of a spectrographic components. In some embodiments, the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.

Described herein are methods comprising: receiving a tagged recording of spontaneous speech from a subject, wherein the tagged recording is associated with a tagged brain image; using a machine learning speech quantifying classifier to produce a tagged speech quantifying score based at least in part on the spontaneous speech; generating tagged comprehension feature values from the tagged recordings of spontaneous speech; using a machine learning comprehension classifier to produce a tagged comprehension score based at least in part on the tagged comprehension feature values, the comprehension classifier trained using training comprehension feature values and corresponding training comprehension scores; determining an aphasia classification based on at least one of the tagged speech quantifying score and the tagged comprehension score; tagging a brain image of a plurality of brain images with a corresponding aphasia tagging classification, to create a plurality of tagged brain images; and training, with the tagged brain images, a brain image aphasia classifier configured to i) receive brain images and ii) return an aphasia classification.

In some embodiments, the method further comprises: generating tagged speech quantifying feature values from the spontaneous speech and wherein using the machine learning speech quantifying classifier to produce the tagged speech quantifying score based at least in part on the spontaneous speech comprises using the machine learning speech quantifying classifier to produce the tagged speech quantifying score based at least in part on the tagged speech quantifying feature values, the machine learning speech quantifying classifier trained using training tagged speech quantifying feature values and corresponding tagged training speech quantifying scores. In some embodiments, using a machine learning comprehension classifier to produce a tagged comprehension score based at least in part on the tagged comprehension feature values comprises using a machine learning comprehension classifier to produce a tagged comprehension score based at least in part on the tagged comprehension feature values and on the tagged speech quantifying score. In some embodiments, the machine learning speech quantifying classifier is trained using tagged training spontaneous speech and corresponding tagged training speech quantifying scores. In some embodiments, the determining an aphasia classification based on at least one of the tagged speech quantifying score and the tagged comprehension score further comprises submitting the tagged speech quantifying score and the tagged comprehension score to an aphasia classifier to receive a tagged aphasia classification, the aphasia classifier trained using tagged training speech quantifying scores and tagged training comprehension scores and corresponding training aphasia classifications. In some embodiments, determining an aphasia classification comprises determining a set of tagged aphasia confidence values for different types of aphasia and then using those tagged aphasia confidence values to select an aphasia classification. In some embodiments, the method generates tagged comprehension feature values from the spontaneous speech and submits the tagged comprehension feature values to a comprehension classifier to produce a tagged comprehension score only if the tagged speech quantifying score exceeds a threshold. In some embodiments, the method further comprises: receiving an initial recording, wherein the initial recording comprises i) a video recording of the subject or ii) an audio recording of the subject; and generating a text transcript from the initial recording. In some embodiments, the tagged speech quantifying feature values comprise one or more of: sounds per minute; words per minute; unique words per minute; a verb list; a count of a number of verbs; a proportion of valid words that are verbs; a noun list; a count of a number of nouns; a proportion of valid words that are nouns; a count of number of times a word was repeated twice in a row; and a representation of a spectrographic components. In some embodiments, the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group. In some embodiments, the method further comprises: receiving a brain image from a subject; using the brain image classifier to produce an aphasia classification, wherein the brain image classifier is trained according to the methods described herein.

Described herein are systems comprising: one or more computers and one or more storage devices on which are stored instructions that are operable, when executed by the one or more computers, to cause the one or more computers to perform operations comprising: receiving a recording of spontaneous speech from a subject; using a machine learning speech quantifying classifier to produce a speech quantifying score based at least in part on the spontaneous speech; generating comprehension feature values from the spontaneous speech; using a machine learning comprehension classifier to produce a comprehension score based at least in part on the comprehension feature values, the comprehension classifier trained using training comprehension feature values and corresponding training comprehension scores; determining an aphasia classification based on at least one of the speech quantifying score and the comprehension score; and using the aphasia classification to process at least one of the spontaneous speech and the subject.

In some embodiments, the system further comprises: generating speech quantifying feature values from the spontaneous speech and wherein using the machine learning speech quantifying classifier to produce the speech quantifying score based at least in part on the spontaneous speech comprises using the machine learning speech quantifying classifier to produce the speech quantifying score based at least in part on the speech quantifying feature values, the machine learning speech quantifying classifier trained using training speech quantifying feature values and corresponding training speech quantifying scores. In some embodiments, using a machine learning comprehension classifier to produce a comprehension score based at least in part on the comprehension feature values comprises using a machine learning comprehension classifier to produce a comprehension score based at least in part on the comprehension feature values and on the speech quantifying score. In some embodiments, the machine learning speech quantifying classifier is trained using training spontaneous speech and corresponding training speech quantifying scores. In some embodiments, the determining an aphasia classification based on at least one of the speech quantifying score and the comprehension score further comprises submitting the speech quantifying score and the comprehension score to an aphasia classifier to receive an aphasia classification, the aphasia classifier trained using training speech quantifying scores and training comprehension scores and corresponding training aphasia classifications. In some embodiments, determining an aphasia classification comprises determining a set of aphasia confidence values for different types of aphasia and then using those confidence values to select an aphasia classification. In some embodiments, the system further comprises: receiving an initial recording, wherein the initial recording comprises i) a video recording of the subject or ii) an audio recording of the subject; and generating a text transcript from the initial recording. In some embodiments, the speech quantifying feature values comprise one or more of: sounds per minute; words per minute; unique words per minute; a verb list; a count of a number of verbs; a proportion of valid words that are verbs; a noun list; a count of a number of nouns; a proportion of valid words that are nouns; a count of number of times a word was repeated twice in a row; and a representation of a spectrographic components. In some embodiments, the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.

The subject matter described in this specification can be implemented in particular embodiments so as to realize one or more of the following advantages. In one embodiment, an advantage of the methods, systems, and computer-readable storage media described herein is that the methods, systems, and computer-readable storage media can be implemented by a lay person. Traditionally, aphasia assessment is performed by neuropsychologist or speech pathologist with specific training in aphasia assessments. The aphasia assessment methods described herein can be implemented by a lay person, reducing the likelihood of aphasia assessment backlogs and patient wait times, which may be present in other processes. The technician administering the aphasia assessment is there to help start the administration and/or recording device, but need not spend time diagnosing the patient, which can reduce cost. Further, this advantage of not requiring highly trained staff allows the technology to be used in remote locations with less specialized staff, and extend the technology to patients who may otherwise not be able to interact with a highly trained expert. An additional advantage of the methods, systems, and computer-readable storage media described herein is the standardization of the administration of aphasia assessments. When an assessment is administered by a person, even a highly trained person, differences in training and/or personal style may produce inconsistent classifications/diagnoses. The aphasia classifier described herein can reduce or eliminate the diagnosis inconsistencies within and between administrators. The technology of computer-assisted aphasia diagnosis is advanced by the subject matter described in this specification.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
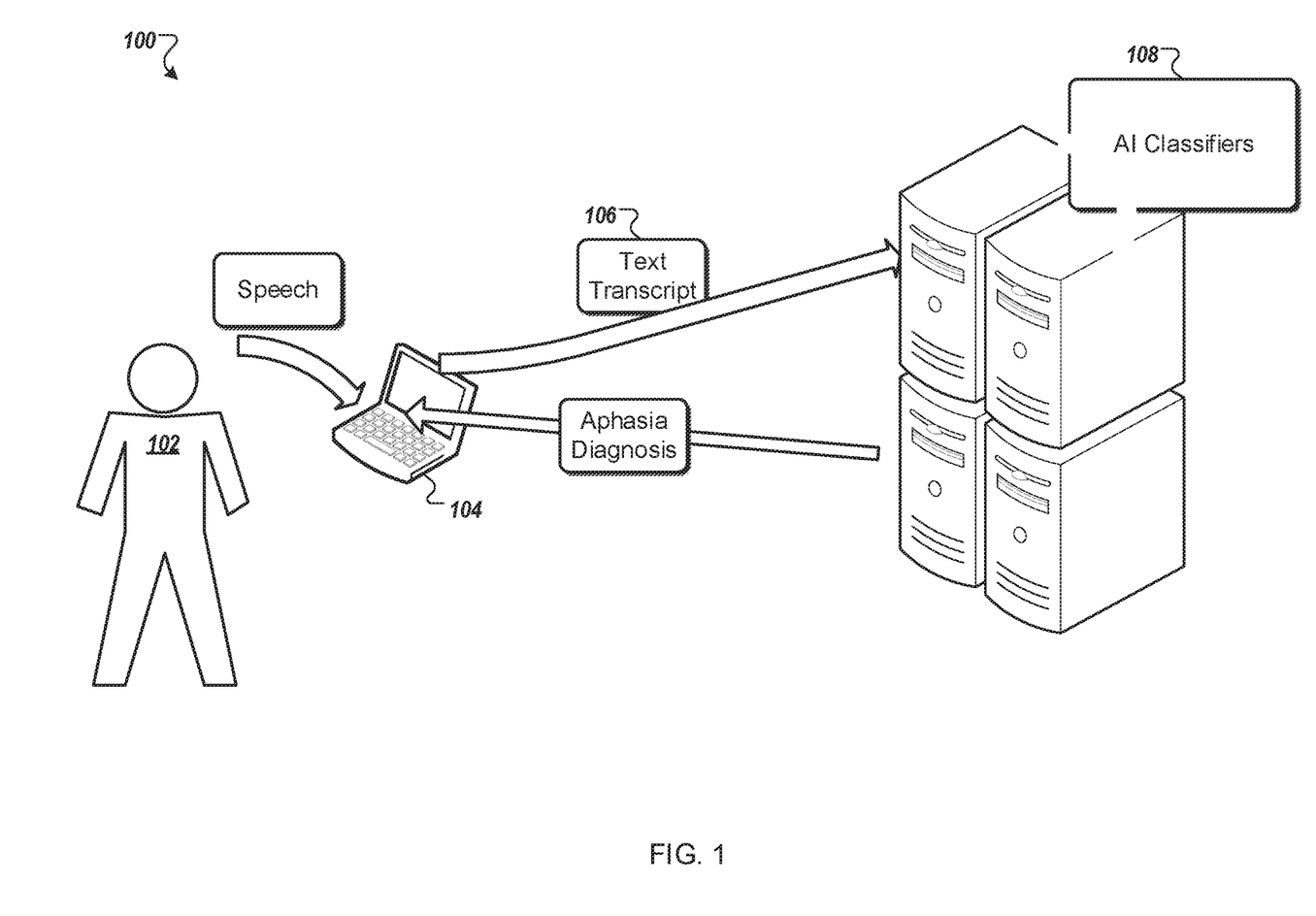
FIG. 1 shows an example system, wherein a patient produces spontaneous speech in response to a prompt. The speech, if a recording, can be transcribed into word series and fed through the machine learning classifiers described herein. The classifiers produce an aphasia confidence value that is used to determine an aphasia classification.

Methods of Using Machine Learning Trained Classifiers to Process Spontaneous Speech for Aphasia Classification FIG. 1 shows an exemplary system 100 used for performing an aphasia assessment within the context of a neuropsychological test. In the system 100, a patient 102 is recorded performing a spontaneous speech task. For example, the patient is prompted by a computer program or a clinician/assistant to describe how to make a peanut butter and jelly sandwich. The patient's spontaneous speech to the speech prompt is recorded by a recording device 104. The recording of the patient's speech is transcribed to produce a text transcript 106 of the recording. In an alternative embodiment, the spontaneous speech can be converted immediately to text as the speech is uttered using a speech to text processing system. The text transcript is provided as input to a series of classifiers 108. The output of classifiers is provided as input to an aphasia classifier 420, the outcome of which is an aphasia classification. In this process, the recording device 104 can perform the text transcription and machine learning steps of the process. The recording device 104 can process the spontaneous speech locally or it can send the patient's recording to a remote system (e.g., a server, a cloud service), wherein the remote system can perform the text transcription and machine learning steps of the process. The aphasia assessment can be performed independently of other tests (e.g., neuropsychological tests). Alternatively, the aphasia assessment can be performed prior to the selection and/or performance of other tests (e.g., neuropsychological tests).

Figure 2:
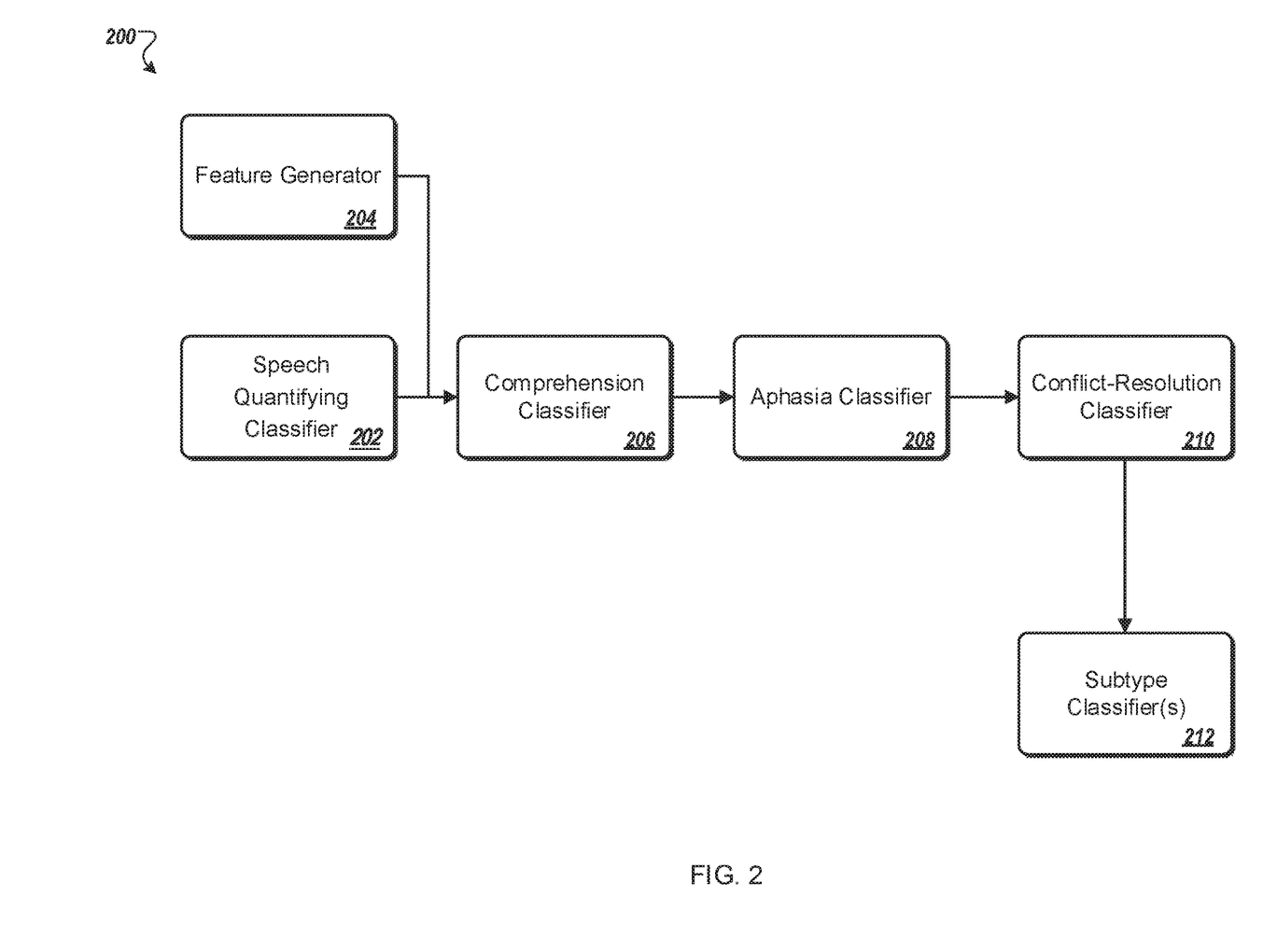
FIG. 2 shows a flowchart of stacked machine learning classifiers that can be used to produce an aphasia classification.

FIG. 2 is a computer pipeline 200 outlining exemplary classifiers used by computer systems to generate and store data to record an aphasia classification in computer memory. In general, classifiers following machine learning procedures include learning a mapping between a feature vector and an outcome (e.g. positive or negative). For convenience, the classifiers of 200 will be described as being performed by a system of one or more computers, located in one or more locations, and programmed appropriately in accordance with this specification. For example, the system designed to perform the process of FIG. 1, appropriately programmed, can perform the process 200. For example, speech quantifying feature values can be extracted from the text transcript 106 of a patient's recording and entered into a speech quantifying classifier 202, wherein the output of the speech quantifying classifier 202 can be used as input for a comprehension classifier 206. Optionally, comprehension feature values produced by a feature generator 204 can also be used as input for a comprehension classifier 206. The output of the comprehension classifier 206 can be used as input for an aphasia classifier 208, wherein the output of the aphasia classifier is an aphasia classification. Optionally, the output of the aphasia classifier 208 can be used as input to a conflict-resolution classifier 210. The conflict-resolution classifier can compare aphasia confidence values given to a plurality of possible aphasia types and select the possible aphasia type with the highest confidence value. Optionally, the output of the aphasia classifier 208 or the conflict resolution classifier 210 can serve as input for a subtype classifier 212. The subtype classifier 212 can provide additional detail to the possible aphasia type identified by the aphasia classifier 208 or the conflict resolution classifier 210 by identifying a subtype of the identified possible aphasia type or by providing additional details about the possible aphasia type.

Figure 3:
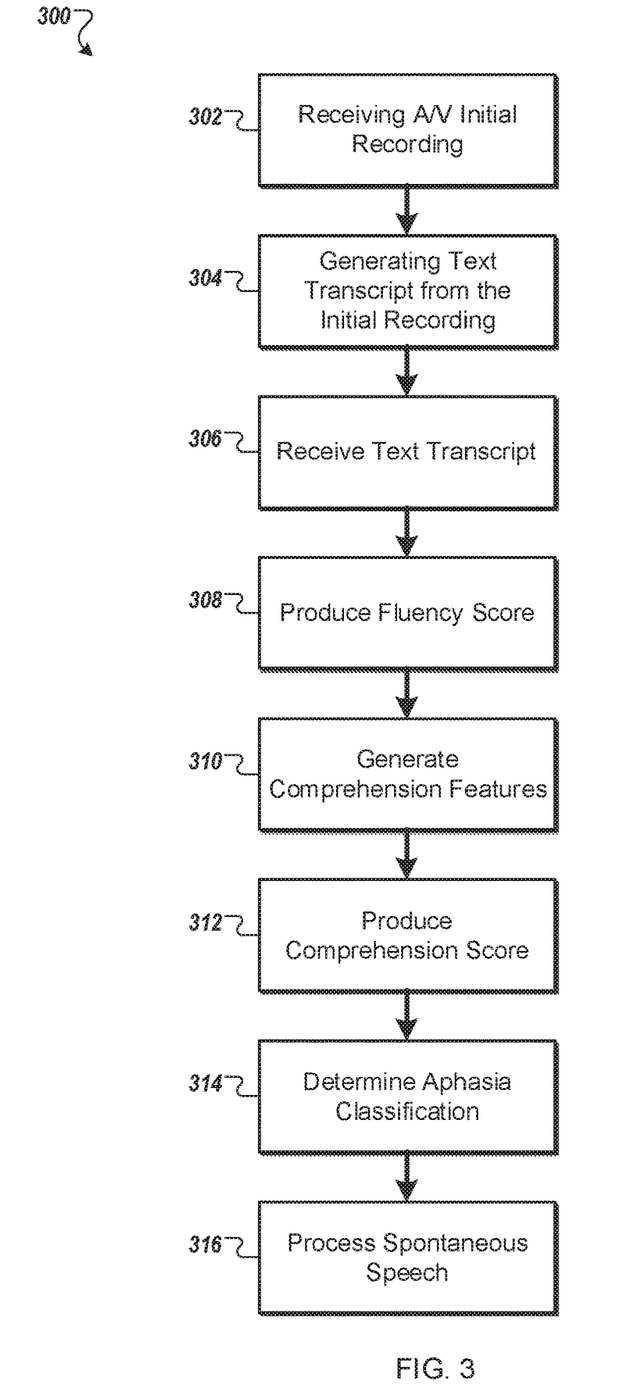
FIG. 3 shows a flowchart of an exemplary process for determining an aphasia classification from an initial recording.
Figure 4:
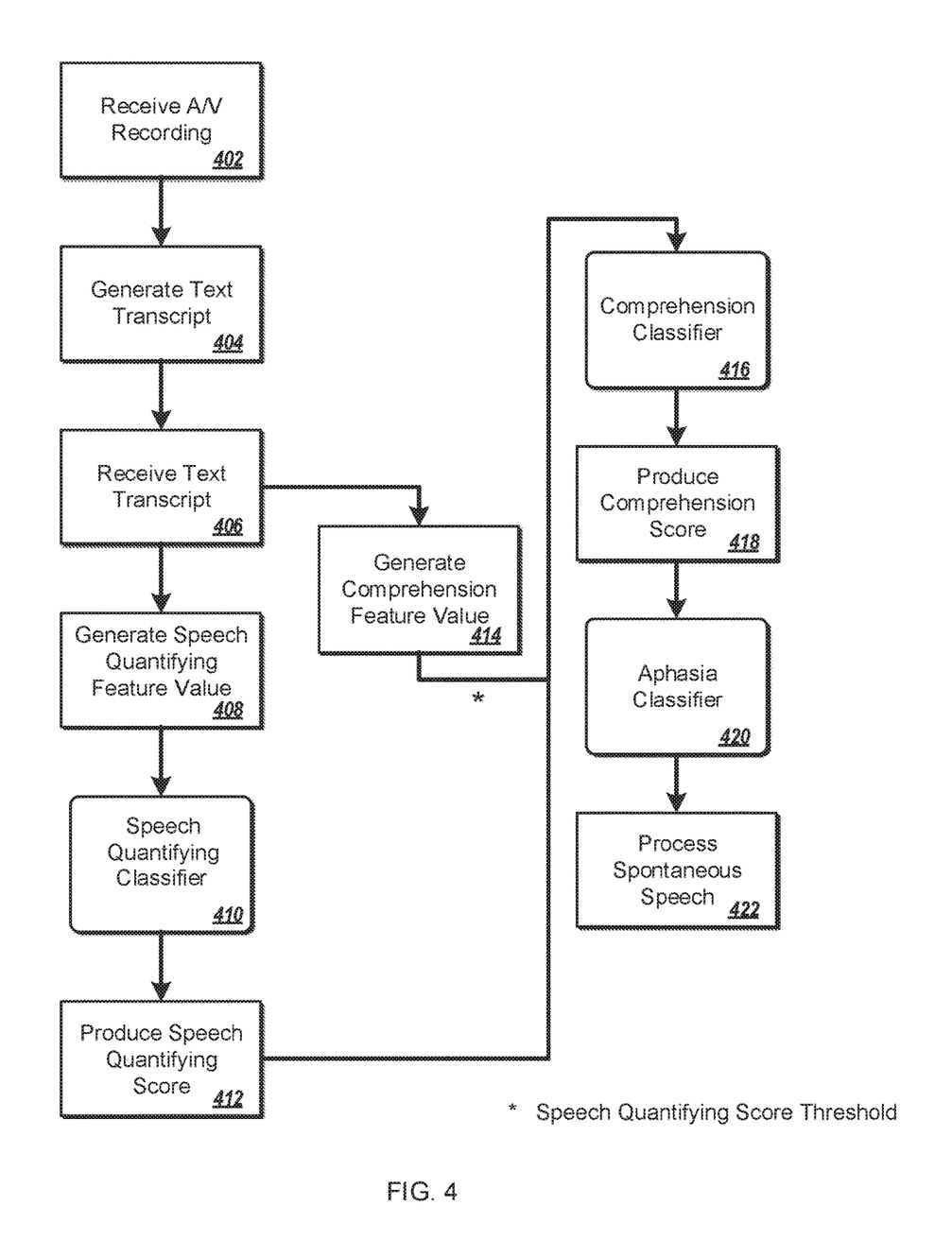
FIG. 4 shows a flowchart of another exemplary process for determining an aphasia classification.

FIG. 3 and FIG. 4 are flowcharts of an exemplary method of those described herein. The method can be carried out on a device or on multiple devices. For example, one possible configuration of the steps to process a spontaneous speech recording of a possible aphasia patient can include receiving an initial recording 302, wherein the initial recording 302 is an audio or video recording, and generating a text transcript 304 from the initial recording 302. For example, generating a text transcript 304 from the initial recording 302 can include splitting the audio/video recording into 30 second chunks around moments of silence, wherein the chunks are split between words, and the audio chunks are transcribed into a word series. Further, features can be identified and extracted from the text transcript 306. For example, features can include sounds per minute, words per minute, unique words per minute, a verb list, a count of a number of verbs, a proportion of valid words that are verbs, a noun list a count of a number of nouns, a proportion of valid words that are nouns, a count of number of times a word was repeated twice in a row, and a representation of spectrographic components.

A speech quantifying assessment can be performed on the text transcript 306 by generating speech quantifying feature values 408 which can then be used in a machine learning speech quantifying classifier 410 to produce a speech quantifying score 308, 412. The speech quantifying score 308, 412 can be based at least in part on speech quantifying feature values 408. A speech quantifying score 308, 412 can be identified in units of words-per-specified time period. Speech quantifying feature values 408 can include sounds per minute, words per minute, unique words per minute, a verb list, a count of a number of verbs, a proportion of valid words that are verbs, a noun list a count of a number of nouns, a proportion of valid words that are nouns, a count of number of times a word was repeated twice in a row, and a representation of spectrographic components. The machine learning speech quantifying classifier 410 can be trained using training spontaneous speech and corresponding training speech quantifying scores. The machine learning speech quantifying classifier 410 can be trained on a first training set that includes recordings that have been tagged with corresponding training speech quantifying scores. In certain implementations, one can train a XGBoost model to classify Broca's aphasia based on the speech quantifying features noted above. In other implementations, one of a variety of regressor models can be used. A comprehension assessment can be performed on the text transcript 306 by generating comprehension feature values 310, 414 which can then be used in a machine learning comprehension classifier 416 to produce a comprehension score 312, 418. In some embodiments, only if the speech quantifying score 308, 412 exceeds a pre-specified threshold are the comprehension feature values 414 from the text transcript 416 submitted to a comprehension classifier 416 to produce a comprehension score 418. Comprehension features values can include sounds per minute, words per minute, unique words per minute, a verb list, a count of a number of verbs, a proportion of valid words that are verbs, a noun list, a count of a number of nouns, a proportion of valid words that are nouns, a count of number of times a word was repeated twice in a row, and a representation of a spectrographic components. The machine learning comprehension classifier 416 can be trained using training comprehension feature values and corresponding training comprehension scores. In some embodiments, the machine learning comprehension classifier 416 can be trained on a second training set that comprises training speech quantifying scores and a plurality of training feature values that have been tagged with corresponding training comprehension scores.

In certain implementations, the comprehension assessment can include transcribing audio by estimating the overall global noise/audio to identify portion of silences, splitting the spontaneous speech audio into chunks (e.g., of between about 15 to 45 seconds) around those moments of silence (i.e., splitting the audio into chunks between words), and transcribing the audio chunks into word series. The system can then tokenize words using e.g., Keras text processing and train a bi-directional LSTM on the tokenized text (e.g., using a maximum sequence length of 30 and an embedding dimension of 30).

An aphasia classification can be performed by submitting at least one of the speech quantifying score 308, 412 and the comprehension score 312, 418 to a machine learning aphasia classifier 420 to produce a set of aphasia confidence values for different types of aphasia. In some embodiments, the speech quantifying score 308, 412 is submitted to the aphasia classifier 420. In some embodiments, the comprehension score 418 is submitted to the aphasia classifier 420. In some embodiments, both the speech quantifying score 308, 412 and the comprehension score 418 is submitted to the aphasia classifier 420. The aphasia classifier 420 can then use those confidence values to select an aphasia classification. The machine learning aphasia classifier 420 can be trained using training speech quantifying scores and training comprehension scores and corresponding training aphasia classifications. In some embodiments, the machine learning aphasia classifier 420 can be trained on a third training set that includes training speech quantifying scores, training comprehension score, and a plurality of training feature values that have been tagged with corresponding training aphasia classifications.

In some embodiments, the aphasia classification can be submitted to a sub-type classifier 212, wherein the sub-type classifier 212 provides a sub-type classification. In some embodiments, the sub-type classification can be a sub-type of the aphasia classification identified by the aphasia classifier 420. In some embodiments, the sub-type classifier 212 can provide additional details regarding the aphasia classification.

The aphasia classification, and optionally the sub-type classification, produced by the methods, systems, and/or computer-readable media described herein can be used to determine appropriate recommendations for follow-on neuropsychological tests based on the patient's aphasia classification. The follow-on neuropsychological tests can be administered via the same device 104 used to record the patient's spontaneous speech, or a different device. The follow-on neuropsychological test recommendations can be performed immediately after the aphasia classification is determined, or the recommendations can be saved to be pursed at another time.

In certain implementations, one can stack the speech quantifying and comprehension classifiers as follows: 1) perform an initial assessment of fluency (e.g., speech quantification) (providing a score as to whether subject is likely to have an a non-fluent aphasia) using speech quantifying classifier; 2) if the subject has high fluency (e.g., non-fluent aphasia score is <0.5), then assess comprehension using comprehension classifier; and 3) score the subject on degree of fluency, degree of comprehension, and categorize the subject as either Broca's Aphasia, Wernicke's Aphasia, or other.

Methods of Training Machine Learning to Process Spontaneous Speech for Aphasia Classification Described previously is the use of technology for the purposes of classifying a new patient's speech patterns into one or more aphasias. That is, this technology can help to process a subject more efficiently. However, technology described in this document can also be used for other purposes. One of those other use cases is now described.

This technology can be used to aid in the training of machine-learning classifiers that are to be configured to classify brain images into one or more aphasia classifications. In this use case, a dataset of brain images may be collected from a wide range of people, including people identified as having an aphasia and people not identified as having an aphasia (or identified as not having an aphasia). In some embodiments, the people may be recorded in responding to a structured prompt, in other embodiments the people may be speaking without the aid of a structured prompt. Some of these people may be aphasia patients, but importantly some of the people are known or expected to have no aphasia. This is done so that the dataset represents both or all possible outcomes of an aphasia classifier, which may advantageously allow for a well-trained classifier to be created. As will be understood, many machine-learning training processes have increased accuracy if many samples of all possible classifications are available.

One or more of the recordings may be subjected to the machine learning based aphasia classification processes described in this document. The result of which is the creation of a dataset with at least three fields: i) a brain image of a person; ii) an aphasia classification for the same person, which can include a no-aphasia option; and iii) a unique identifier for the person. The unique identifier may be obfuscated to protect privacy, as its purpose may be limited to ensuring matches between the brain images and the aphasia classifications, and the unique identifiers may be deleted or never used, depending on the particular implementation details of the data storage systems in use. In some embodiments, other fields may be used. For example, another field for an expert aphasia assessment can be added. This may be of value, for example, if the expert assessments of aphasia are different than those produced by the classifiers, having different levels of accuracy, different conclusions, or different levels of sensitivity, for example.

With this data set, the aphasia classification may be used as a tag that describes the corresponding brain image. That is to say, for a person with Broca's Aphasia, the data set may store an image of that person's brain along with a tag indicating Broca's Aphasia. For another person with no aphasia, the data set may store an image of that other person's brain a tag of No-Aphasia.

This dataset may be used in the training on one or more classifiers that receive as input a brain image and produce as output an aphasia classification. In this way, the technology described here can be used for the generation of aphasia classifications (e.g. aphasia diagnoses) that do not require any speech recordings for a new, incoming patient. Instead, the patient's brain may be imaged and the image provided directly to an aphasia classifier.

Figure 5:
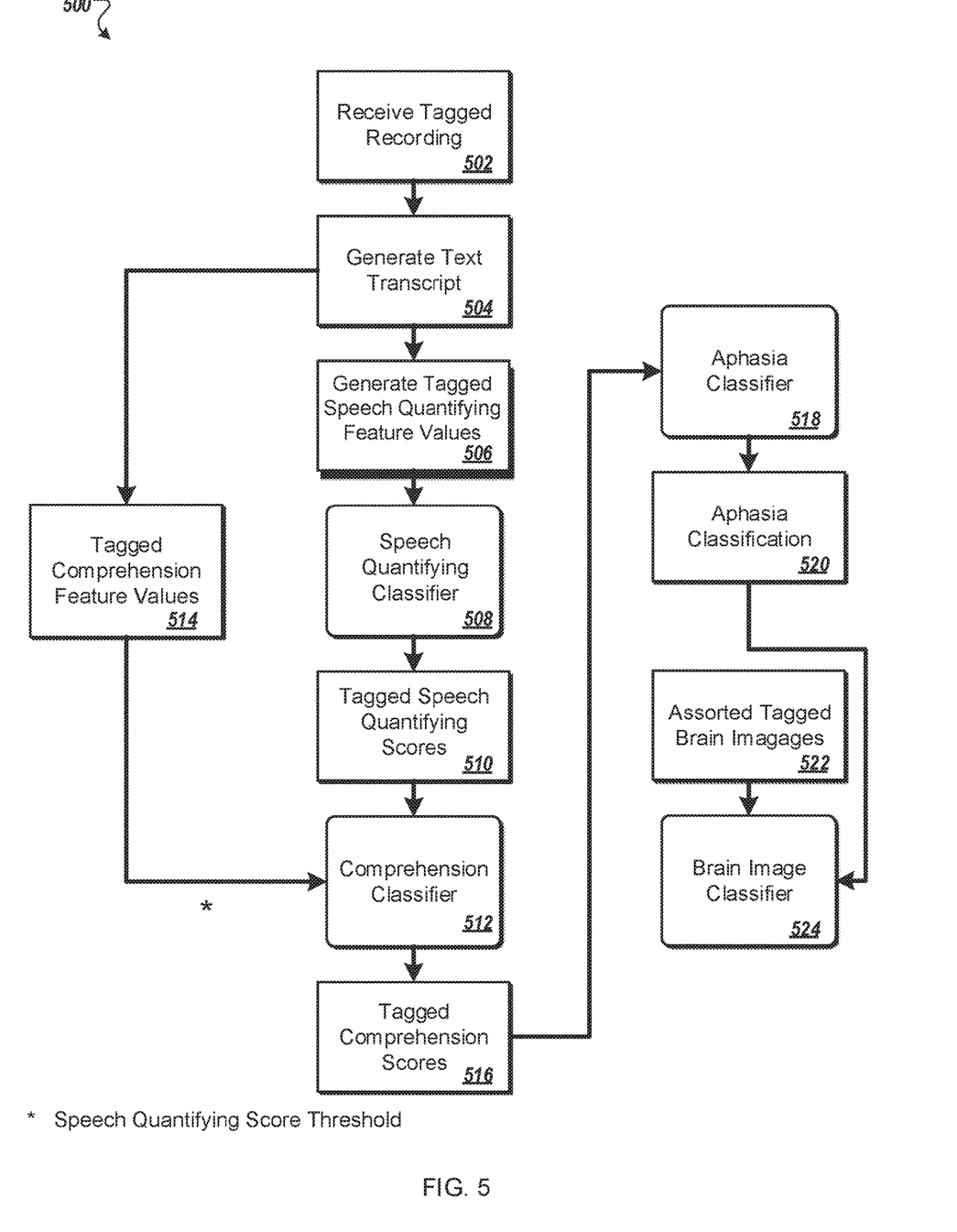
FIG. 5 shows a flowchart of an exemplary process for training one or more brain image aphasia classifiers as described herein.

FIG. 5 is a flow chart of an exemplary method for training a machine learning aphasia classifier as described herein, wherein the aphasia classifier 518 can be used to provide an aphasia classification (e.g., aphasia diagnosis) that is associated with a brain scan (e.g., an fMRI, EEG). The brain scan (e.g., fMRI) may indicate where the brain may be damaged. The result of associating the output of the aphasia classifier described herein with brain scans of damaged brains can be to be able to predict if a person is likely to have aphasia, and if so what type of aphasia, based on a brain scan, without having to have the person perform an aphasia assessment as is traditionally required. One possible configuration of the steps to train one or more classifiers that receive as input a brain image can include receiving a tagged recording 502, wherein the tagged recording 502 is an audio or video recording, and generating a text transcript 504 from the tagged recording 502, wherein the tagged recording 502 corresponds to a tagged brain image. Similar to the above, generating a text transcript 504 from the tagged recording 502 can include splitting the audio/video recording into 30 second chunks around moments of silence, wherein the chunks are split between words, and the audio chunks are transcribed into a word series. Further, features can be identified and extracted from the text transcript 504. For example, features can include sounds per minute, words per minute, unique words per minute, a verb list, a count of a number of verbs, a proportion of valid words that are verbs, a noun list a count of a number of nouns, a proportion of valid words that are nouns, a count of number of times a word was repeated twice in a row, and a representation of spectrographic components.

A speech quantification assessment can be performed on the text transcript 504 associated with a brain image by generating tagged speech quantifying feature values 506 which can then be used in a machine learning speech quantifying classifier 508 to produce a tagged speech quantifying score 510. The tagged speech quantifying score 510 can be based at least in part on tagged speech quantifying feature values 506. A tagged speech quantifying score 510 can be identified in units of words-per-specified time period. Tagged speech quantifying feature values 506 can include sounds per minute, words per minute, unique words per minute, a verb list, a count of a number of verbs, a proportion of valid words that are verbs, a noun list a count of a number of nouns, a proportion of valid words that are nouns, a count of number of times a word was repeated twice in a row, and a representation of spectrographic components. The machine learning speech quantifying classifier 508 can be trained using tagged training spontaneous speech and corresponding tagged training speech quantifying scores. The machine learning speech quantifying classifier 508 can be trained on a first tagged training set that includes recordings that have been tagged with corresponding tagged training speech quantifying scores.

A comprehension assessment can be performed on the text transcript 504 by generating tagged comprehension feature values 511 which can then be used in a machine learning comprehension classifier 512 to produce a tagged comprehension score 516. In some embodiments, only if the tagged speech quantifying score 510 exceeds a pre-specified threshold are the tagged comprehension feature values 514 from the text transcript 504 submitted to a comprehension classifier 512 to produce a tagged comprehension score 516. Tagged comprehension features values can include sounds per minute, words per minute, unique words per minute, a verb list, a count of a number of verbs, a proportion of valid words that are verbs, a noun list, a count of a number of nouns, a proportion of valid words that are nouns, a count of number of times a word was repeated twice in a row, and a representation of a spectrographic components. The machine learning comprehension classifier 512 can be trained using tagged training comprehension feature values and corresponding tagged training comprehension scores. In some embodiments, the machine learning comprehension classifier 512 can be trained on a second training set that comprises tagged training speech quantifying scores and a plurality of tagged training feature values that have been tagged with corresponding tagged training comprehension scores.

An aphasia classification can be performed by submitting at least one of the tagged speech quantifying score 510 and the tagged comprehension score 516 to a machine learning aphasia classifier 518 to produce a set of tagged aphasia confidence values for different types of aphasia. In some embodiments, the tagged speech quantifying score 510 is submitted to the aphasia classifier 518. In some embodiments, the tagged comprehension score 516 is submitted to the aphasia classifier 518. In some embodiments, both the tagged speech quantifying score 510 and the tagged comprehension score 516 is submitted to the aphasia classifier 518. The aphasia classifier 518 can then use those tagged confidence values to select an aphasia classification. The machine learning aphasia classifier 518 can be trained using tagged training speech quantifying scores and tagged training comprehension scores and corresponding tagged training aphasia classifications. In some embodiments, the machine learning aphasia classifier 518 can be trained on a third training set that includes tagged training speech quantifying scores, tagged training comprehension score, and a plurality of tagged training feature values that have been tagged with corresponding tagged training aphasia classifications.

In an alternative embodiment, a brain image aphasia classifier 524 can be trained by submitting a tagged brain image (e.g., a brain scan) 522 and a tagged aphasia classification 520, wherein the tagged brain image 522 is associated with the tagged aphasia classification 520. In some embodiments, the tagged brain image 522 and tagged aphasia classification 520 is from a person that does not have aphasia. In some embodiments, a brain image can be submitted to the brain image aphasia classifier 524, wherein the brain image aphasia classifier 524 provides an aphasia classification.

Types of Aphasia

Aphasia is an acquired impairment, due to brain injury, of the production or comprehension of speech. Aphasia differs from dysarthria, which is the inability to move the muscles of the mouth/tongue to produce speech. The brain injury that causes aphasia can include any injury to the brain. Typically, the brain injury is a result of a stroke or a series of strokes, although the brain injury can include traumatic brain injury, injury as a result of an infection, disease, or tumor, or any other type of injury to the brain. There are different types of aphasia which commonly correspond to the location of brain injury in a particular individual. The brain injury, including the location of the brain injury, can sometimes be confirmed by medical imaging (e.g., MRI, fMRI, or CT scan). Sometimes an individual exhibits one type of aphasia, sometimes an individual exhibits features of more than one type of aphasia. Typically, a neuropsychologist, speech-language pathologist (SLP), or other cognitive science professional uses neuropsychological test to determine the type(s) and degree of an affected individual's aphasia. Additionally, the SLP or neuropsychologist also assesses what types of treatments or therapies might be appropriate for a particular affected individual.

There are two main branches of aphasia: nonfluent aphasia, where an affected individual struggles to produce the intended words and may omit words or produce very short sentences, and fluent aphasia, where an affected individual can typically speak in sentences that sound like normal speech, however, upon closer inspection a portion of the word sounds are not correct or are made-up entirely. Within nonfluent aphasia, major recognized types include global aphasia, mixed transcortical aphasia, Broca's aphasia, and trancortical motor aphasia. Within fluent aphasia, major recognized types include Wernicke's aphasia, transcortical sensory aphasia, conductions aphasia, anomic aphasia. There are subtypes of aphasia that may or may not fall within the major recognized types, (e.g., auditory verbal agnosia, foreign accent syndrome). Additionally, much research has been done to elucidate and categorize various paraphasias.

Global Aphasia

Global aphasia is the most severe form of aphasia. An affected individual typically presents with little to no spoken language, and also lack the ability to read or write. This type of aphasia is typically caused by a large injury affecting a large portion of the left side of the brain. This is sometimes the case with global aphasia caused by stroke (e.g., occlusion of the left middle cerebral artery). Symptoms of global aphasia may improve after the injury or they may not. Commencing of language therapy soon after the injury has the potential to help the affected individual recover some language functioning.

Mixed Transcortical Aphasia

Mixed transcortical aphasia (sometimes referred to as isolation aphasia) exhibits many of the characteristics of global aphasia (e.g., little to no spoken language, lack of ability to read or write), however, the affected individual's ability to repeat short spoken phrases is preserved. Therefore, affected individuals often do not voluntarily produce speech sounds, but can reproduce short phrases spoken to the affected individual (sometimes referred to as echoalia). The affected individual does not demonstrate comprehension of the speech they repeat. Similar to global aphasia, this type of aphasia is typically caused by a large injury affecting a large portion of the left side of the brain (e.g., an occlusion of the left middle cerebral artery).

Broca's Aphasia

Broca's aphasia (sometimes referred to as expressive aphasia) is a type of non-fluent aphasia where vocabulary is limited, and speech occurs in short, choppy phrases. The speech generally include the important nouns and verbs, but typically leaves out prepositions and articles. The affected individual can retain the ability to read as well as understand straightforward, non-ambiguous speech, but understanding complex, ambiguous speech (e.g., long sentences with passive voice) and writing may be more difficult. This type of aphasia typically occurs when injury is sustained to Broca's area (e.g., left inferior frontal gyms). Additionally, Broca's area is associated with speech-associated gestures, and thus Broca's aphasia can occur in those individuals that communicate using sign-language (e.g., an affected person that communicates using sign-language may only sign 2 to 4 word phrases comprising important nouns and verbs).

Transcortical Motor Aphasia

Transcortical motor aphasia (TMoA; sometimes referred to as commissural dysphasia or white matter dysphasia) is a type of non-fluent aphasia characterized by effortful output of short, choppy phrases, but wherein the ability to repeat longer phrases and auditory comprehension is retained. Additionally, the affected individual may also present with a number of paraphasias (described below). Typically, in transcortical motor aphasia, the anterior superior frontal lobe in the perisylvian area is damaged, but Broca's area, the arcuate fasciculus, and Wernicke's area are not damaged. Subtypes of transcortical motor aphasia include adynamic aphasia, or sparse speech, and dynamic aphasia, or the difficulty of combining linguistic elements.

Wernicke's Aphasia

Wernicke's aphasia is a type of fluent aphasia (sometimes referred to a receptive aphasia) where the ability to produce connected speech sounds is intact, however the affected individual often cannot grasp the meaning of speech spoken to them and cannot produce speech with context-appropriate meaning, often using non-existent or inappropriate words. Individuals with Wernicke's aphasia typically are not aware that their speech does not possess meaning for the recipient/communication partner and often the speech contains a number of paraphasias. Paraphasias are characteristic of Wernicke's and other fluent aphasias. A paraphasia is a language error associated with the fabrication of unintended syllables, words, or phrases during speech. Types of paraphasia include: phonemic paraphasias, or the substitution or a word or syllable, wherein the spoken word sounds like the intended word; verbal paraphasias, wherein the spoken word is related to the target word by meaning or category; neologisms, or creation of made-up or nonsense words; circumlocution, describing or talking around the target word; and run-on speech. Verbal paraphasia can be further types: coordinate semantic paraphasia, replacing the target word with a word from the same category; associate semantic paraphasia, replacing the target word with a related word but not of the same category; superordinate semantic paraphasia, replacing the target word with the group to which the target word belongs; subordinate semantic paraphasia, replacing the target word with a more specific word in that group; part-whole semantic paraphasia, replacing the part with the whole or the whole with the part (e.g., finger for hand or hand for finger); and visual semantic paraphasia replacing the target word with a word the visually resembles the target word.

Often individuals with Wernicke's aphasia have difficulty in repeating words. Typically, this type of aphasia is associated with damage to the posterior temporal regions of the brain.

Transcortical Sensory Aphasia

Transcortical sensory aphasia (TSA) is a type of fluent aphasia characterized by impaired verbal comprehension, impaired naming, and paraphasia, but preserving the affected individual's ability to repeat words or phrases (i.e., echolalia). The inferior left temporal lobe is often damaged in people with TSA, however, Broca's and Wernicke's areas are usually undamaged in people with TSA. TSA can be difficult to diagnose using medical imaging (e.g., fMRI), and therefore neuropsychological and language processing tests are primarily used to diagnose transcortical sensory aphasia.

Conduction Aphasia

Conduction aphasia (sometimes referred to as association aphasia) is a type of fluent aphasia characterized by intact auditory comprehension, fluent speech production, but difficulty in repeating phrases and frequent paraphasic errors. It is thought that left superior temporal gyms or the left supra marginal gyms or the arcuate fasciculus is damaged in people with conductive aphasia. Since auditory comprehension is relatively intact, conductive paraphasiacs will make a repetitive effort to correct paraphasic errors.

Anomic Aphasia

Anomic aphasia (sometimes referred to as dysnomia, nominal aphasia, or amnesic aphasia) is a type of fluent aphasia the inability to articulate the specific nouns and verbs the person is attempting to express. Often the affected individual uses vague words or tries to describe the word they are trying to find. Reading and reading comprehension are relatively preserved, but the difficulty in finding words appears in both speech and writing. Anomia, or the inability to articulate words, is present in every type of aphasia, and anomic aphasia is the type of aphasia in which anomia is the primary symptom, such that speech fluency, repetition, comprehension, and grammatical speech remain relatively intact. Anomic aphasia may be the result of injury to any number of places in the left hemisphere, but it appears that damage to the left parietal lobe may typically be implicated.

Primary Progressive Aphasia

Primary progressive aphasia (PPA) may present as either a fluent aphasia or a non-fluent aphasia, however instead of the brain injury being a relatively acute brain injury (e.g., stroke or traumatic brain injury), the underlying brain injury is neurodegenerative disease. Since neurodegenerative disease typically progresses (i.e., the affected individual becomes more impaired), PPA may begin mild aphasia symptoms, which steadily get worse over time (this is in possible contrast to aphasias resulting from stroke or TBI, which may improve over time). PPA may be caused by, or a feature of, other neurodegenerative diseases (e.g., Alzheimer's disease or Frontotemporal Lobar Degeneration) or PPA can present independently of other neurodegenerative diseases. Recognized subtypes of PPA are Progressive Non-Fluent Aphasia (PNFA), Semantic Dementia (SD), and Logopenic Progressive Aphasia (LPA).

Neuropsychological Tests

Neuropsychologists, clinicians, and sometimes patients administer computerized neuropsychological tests for a variety of purposes. Computerized neuropsychological testing, as opposed to non-computerized testing, provides a number of advantages including random presentation of test components, standardization of presentation of the neuropsychological tests, and, ability analyze and/or interpret test results without formal neuropsychological training.

Many traditional neuropsychological tests have been adapted for computer use and still others have been developed specifically for computerized neuropsychological testing. Non-limiting examples of neuropsychological tests include Ammons Quick Test, Aphasia Tests (e.g., Reitan-Indiana Aphasia Screening Test, Boston Diagnostic Aphasia Examination, Comprehensive Aphasia Test, Multilingual Aphasia Examination, Western Aphasia Battery), Beck Depression or Anxiety Scales, Bender Visual Motor Gestalt Test, Boston Naming Test, California Verbal Learning Test, Cambridge Neuropsychological Test Automated Battery, CDR Computerized Assessment System, Clinical Dementia Rating, CNS Vital Signs, Cognitive Assessment Screening Instrument, Cognitive Function Scanner, Cognitive Symptom Checklists, Cognistat (The Neurobehavioral Cognitive Status Examination), CogScreen: Aeromedical Edition, Continuous Performance Test, Controlled Oral Word Association Test, d2 Test of Attention, Dean-Woodcock Neuropsychology Assessment System, Delis-Kaplan Executive Function System, Dementia Rating Scale, Digit Vigilance Test, Figural Fluency Test, Finger Tapping (Oscillation) Test, General Practitioner Assessment of Cognition, Grooved Pegboard, Halstead Category Test, Halstead-Reitan Neuropsychological Battery, Hayling and Brixton Tests, Hooper Visual Organization Test, Iowa Gambling Task, Kaplan Baycrest Neurocognitive Assessment, Kaufman Functional Academic Skills Test, Kaufman Short Neuropsychological Assessment, Lexical Decision Task, Luria-Nebraska Neuropsychological Battery, MMPI-2 (Minnesota Multiphasic Personality Inventory), Memory Assessment Scales, MicroCog, Millon Clinical Multiaxial Inventory, Mini Mental State Examination, Mooney Problem Checklist, NEPSY, North American Reading Test, Pediatric Attention Disorders Diagnostic Screener, Paced Auditory Serial Attention Test, Paulhus Deception Scales, Personality Adjective Checklist, Quick Neurological Screening Test, Repeatable Battery for the Assessment of Neuropsychological Status, Rey Auditory Verbal Learning Test, Rey Complex Figure Test, Rey 15-item Memory Test, Rey-Osterrieth Complex Figure Test, Rivermead Behavioural Memory Test, Rogers Criminal Responsibility Scale, Rorschach Projective Technique, Ruff Figural Fluency Test, Sensory Screening Test, SCL-90 (Symptom Checklist 90), Shipley Institute of Living Scale, Stroop Test, Symbol Digit Modalities Test, Tactual Performance Test, Test of Memory Malingering, Test of Memory and Learning (TOMAL), Test of Variables of Attention, Thematic Apperception Test, Tower of London, Trail Making Tests A and B, Validity Indicator Profile, Verbal (Word) Fluency Tests (e.g., Controlled Oral Word Association Test, Thurstone Verbal Fluency), Wechsler Adult Intelligence Scale, Wechsler Intelligence Scale for Children, Wechsler Memory Scale, Wechsler Test of Adult Reading, Wide Range Achievement Test, Wisconsin Card Sort Test, Wonderlic Personnel Test, or Word Memory Test.

Computers and Systems for Implementation

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Embodiments

1. A method comprising:
receiving a recording of spontaneous speech from a subject;
using a machine learning speech quantifying classifier to produce a speech quantifying score based at least in part on the spontaneous speech;
generating comprehension feature values from the spontaneous speech;
using a machine learning comprehension classifier to produce a comprehension score based at least in part on the comprehension feature values, the comprehension classifier trained using training comprehension feature values and corresponding training comprehension scores;
determining an aphasia classification based on at least one of the speech quantifying score and the comprehension score; and
using the aphasia classification to process at least one of the spontaneous speech and the subject.

2. The embodiment of claim 1, wherein the embodiment further comprises:
generating speech quantifying feature values from the spontaneous speech and wherein using the machine learning speech quantifying classifier to produce the speech quantifying score based at least in part on the spontaneous speech comprises using the machine learning speech quantifying classifier to produce the speech quantifying score based at least in part on the speech quantifying feature values, the machine learning speech quantifying classifier trained using training speech quantifying feature values and corresponding training speech quantifying scores.

3. The embodiment of claim 1, wherein using a machine learning comprehension classifier to produce a comprehension score based at least in part on the comprehension feature values comprises using a machine learning comprehension classifier to produce a comprehension score based at least in part on the comprehension feature values and on the speech quantifying score.

4. The embodiment of claim 1, wherein the machine learning speech quantifying classifier is trained using training spontaneous speech and corresponding training speech quantifying scores.

5. The embodiment of claim 1, wherein the determining an aphasia classification based on at least one of the speech quantifying score and the comprehension score further comprises submitting the speech quantifying score and the comprehension score to an aphasia classifier to receive an aphasia classification, the aphasia classifier trained using training speech quantifying scores and training comprehension scores and corresponding training aphasia classifications.

6. The embodiment of claim 1, wherein determining an aphasia classification comprises determining a set of aphasia confidence values for different types of aphasia and then using those confidence values to select an aphasia classification.

7. The embodiment of claim 1, wherein the embodiment generates comprehension feature values from the spontaneous speech and submits the comprehension feature values to a comprehension classifier to produce a comprehension score only if the speech quantifying score exceeds a threshold.

8. The embodiment of claim 1, wherein the recording comprises at least one of i) a video recording; ii) an audio recording, and iii) a text transcript.

9. The embodiment of claim 1, the embodiment further comprising:
receiving an initial recording, wherein the initial recording comprises i) a video recording of the subject or ii) an audio recording of the subject; and
generating a text transcript from the initial recording.

10. The embodiment of claim 1, wherein the speech quantifying classifier is trained on a first training set that comprises recordings that have been tagged with corresponding training speech quantifying scores.

11. The embodiment of claim 1, wherein the comprehension classifier is trained on a second training set that comprises training speech quantifying scores and a plurality of training feature values that have been tagged with corresponding training comprehension scores.

12. The embodiment of claim 1, wherein the aphasia classifier is trained on a third training set that comprises training speech quantifying scores, training comprehension scores, and a plurality of training feature values that have been tagged with corresponding training aphasia classifications.

13. The embodiment of claim 1, wherein the speech quantifying score is in units of words-per-specified time period.
14. The embodiment of claim 2, wherein the speech quantifying feature values comprise one or more of:
   sounds per minute;
   words per minute;
   unique words per minute;
   a verb list;
   a count of a number of verbs;
   a proportion of valid words that are verbs;
   a noun list;
   a count of a number of nouns;
   a proportion of valid words that are nouns;
   a count of number of times a word was repeated twice in a row; and
   a representation of a spectrographic components.
15. The embodiment of claim 1, wherein the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.
16. The embodiment of claim 1, the embodiment further comprising:
   selecting, based on the aphasia classification, a subtype classifier from a plurality of subtype classifiers; and
   submitting at least the aphasia classification to the subtype classifier in order to receive a subtype classification.
17. A embodiment comprising:
   receiving a tagged recording of spontaneous speech from a subject, wherein the tagged recording is associated with a tagged brain image;
   using a machine learning speech quantifying classifier to produce a tagged speech quantifying score based at least in part on the spontaneous speech;
   generating tagged comprehension feature values from the tagged recordings of spontaneous speech;
   using a machine learning comprehension classifier to produce a tagged comprehension score based at least in part on the tagged comprehension feature values, the comprehension classifier trained using training comprehension feature values and corresponding training comprehension scores;
   determining an aphasia classification based on at least one of the tagged speech quantifying score and the tagged comprehension score;
   tagging a brain image of a plurality of brain images with a corresponding aphasia tagging classification, to create a plurality of tagged brain images; and
   training, with the tagged brain images, a brain image aphasia classifier configured to i) receive brain images and ii) return an aphasia classification.
18. The embodiment of claim 17, wherein the embodiment further comprises: generating tagged speech quantifying feature values from the spontaneous speech and wherein using the machine learning speech quantifying classifier to produce the tagged speech quantifying score based at least in part on the spontaneous speech comprises using the machine learning speech quantifying classifier to produce the tagged speech quantifying score based at least in part on the tagged speech quantifying feature values, the machine learning speech quantifying classifier trained using training tagged speech quantifying feature values and corresponding tagged training speech quantifying scores.
19. The embodiment of claim 17, wherein using a machine learning comprehension classifier to produce a tagged comprehension score based at least in part on the tagged comprehension feature values comprises using a machine learning comprehension classifier to produce a tagged comprehension score based at least in part on the tagged comprehension feature values and on the tagged speech quantifying score.
20. The embodiment of claim 17, wherein the machine learning speech quantifying classifier is trained using tagged training spontaneous speech and corresponding tagged training speech quantifying scores.
21. The embodiment of claim 17, wherein the determining an aphasia classification based on at least one of the tagged speech quantifying score and the tagged comprehension score further comprises submitting the tagged speech quantifying score and the tagged comprehension score to an aphasia classifier to receive a tagged aphasia classification, the aphasia classifier trained using tagged training speech quantifying scores and tagged training comprehension scores and corresponding training aphasia classifications.
22. The embodiment of claim 17, wherein determining an aphasia classification comprises determining a set of tagged aphasia confidence values for different types of aphasia and then using those tagged aphasia confidence values to select an aphasia classification.
23. The embodiment of claim 17, wherein the embodiment generates tagged comprehension feature values from the spontaneous speech and submits the tagged comprehension feature values to a comprehension classifier to produce a tagged comprehension score only if the tagged speech quantifying score exceeds a threshold.
24. The embodiment of claim 17, wherein the recording comprises at least one of i) a video recording; ii) an audio recording, and iii) a text transcript.
25. The embodiment of claim 17, the embodiment further comprising:
   receiving an initial recording, wherein the initial recording comprises i) a video recording of the subject or ii) an audio recording of the subject; and
   generating a text transcript from the initial recording.
26. The embodiment of claim 17, wherein the speech quantifying classifier is trained on a first training set that comprises recordings that have been tagged with corresponding training speech quantifying scores.
27. The embodiment of claim 17, wherein the comprehension classifier is trained on a second training set that comprises training speech quantifying scores and a plurality of training feature values that have been tagged with corresponding training comprehension scores.
28. The embodiment of claim 17, wherein the aphasia classifier is trained on a third training set that comprises training speech quantifying scores, training comprehension scores, and a plurality of training feature values that have been tagged with corresponding training aphasia classifications.
29. The embodiment of claim 17, wherein the tagged speech quantifying score is in units of words-per-specified time period.
30. The embodiment of claim 18, wherein the tagged speech quantifying feature values comprise one or more of:
   sounds per minute;
   words per minute;
   unique words per minute;
   a verb list;
   a count of a number of verbs;
   a proportion of valid words that are verbs;
   a noun list;
   a count of a number of nouns;
   a proportion of valid words that are nouns;

a count of number of times a word was repeated twice in a row; and a representation of a spectrographic components.

31. The embodiment of claim 17, wherein the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.

32. The embodiment of claim 17, the embodiment further comprising:

selecting, based on the aphasia classification, a subtype classifier from a plurality of subtype classifiers; and submitting at least the aphasia classification to the subtype classifier in order to receive a subtype classification.

33. The embodiment of claim 17, further comprising:

receiving a brain image from a subject;

using the brain image classifier to produce an aphasia classification, wherein the brain image classifier is trained according to the embodiment of claim 17.

34. One or more computer-readable storage media encoded with instructions that, when executed by one or more computers, cause the one or more computers to perform operations comprising:

receiving a recording of spontaneous speech from a subject;

using a machine learning speech quantifying classifier to produce a speech quantifying score based at least in part on the spontaneous speech;

generating comprehension feature values from the spontaneous speech;

using a machine learning comprehension classifier to produce a comprehension score based at least in part on the comprehension feature values, the comprehension classifier trained using training comprehension feature values and corresponding training comprehension scores;

determining an aphasia classification based on at least one of the speech quantifying score and the comprehension score; and using the aphasia classification to process at least one of the spontaneous speech and the subject.

35. The computer-readable storage media of claim 34, further comprising:

generating speech quantifying feature values from the spontaneous speech and wherein using the machine learning speech quantifying classifier to produce the speech quantifying score based at least in part on the spontaneous speech comprises using the machine learning speech quantifying classifier to produce the speech quantifying score based at least in part on the speech quantifying feature values, the machine learning speech quantifying classifier trained using training speech quantifying feature values and corresponding training speech quantifying scores.

36. The computer-readable storage media of claim 34, wherein using a machine learning comprehension classifier to produce a comprehension score based at least in part on the comprehension feature values comprises using a machine learning comprehension classifier to produce a comprehension score based at least in part on the comprehension feature values and on the speech quantifying score.

37. The computer-readable storage media of claim 34, wherein the machine learning speech quantifying classifier is trained using training spontaneous speech and corresponding training speech quantifying scores.

38. The computer-readable storage media of claim 34, wherein determining an aphasia classification based on at least one of the speech quantifying score and the comprehension score further comprises submitting the speech quantifying score and the comprehension score to an aphasia classifier to receive an aphasia classification, the aphasia classifier trained using training speech quantifying scores and training comprehension scores and corresponding training aphasia classifications.

39. The computer-readable storage media of claim 34, wherein determining an aphasia classification comprises determining a set of aphasia confidence values for different types of aphasia and then using those confidence values to select an aphasia classification.

40. The computer-readable storage media of claim 34, wherein the method generates comprehension feature values from the spontaneous speech and submits the comprehension feature values to a comprehension classifier to produce a comprehension score only if the speech quantifying score exceeds a threshold.

41. The computer-readable storage media of claim 34, wherein the recording comprises at least one of i) a video recording; ii) an audio recording, and iii) a text transcript.

42. The computer-readable storage media of claim 34, further comprising:

receiving an initial recording, wherein the initial recording comprises i) a video recording of the subject or ii) an audio recording of the subject; and generating a text transcript from the initial recording.

43. The computer-readable storage media of claim 34, wherein the speech quantifying classifier is trained on a first training set that comprises recordings that have been tagged with corresponding training speech quantifying scores.

44. The computer-readable storage media of claim 34, wherein the comprehension classifier is trained on a second training set that comprises training speech quantifying scores and a plurality of training feature values that have been tagged with corresponding training comprehension scores.

45. The computer-readable storage media of claim 34, wherein the aphasia classifier is trained on a third training set that comprises training speech quantifying scores, training comprehension scores, and a plurality of training feature values that have been tagged with corresponding training aphasia classifications.

46. The computer-readable storage media of claim 34, wherein the speech quantifying score is in units of words-per-specified time period.

47. The computer-readable storage media of claim 34, wherein the speech quantifying feature values comprise one or more of:

sounds per minute;

words per minute;

unique words per minute;

a verb list;

a count of a number of verbs;

a proportion of valid words that are verbs;

a noun list;

a count of a number of nouns;

a proportion of valid words that are nouns;

a count of number of times a word was repeated twice in a row; and a representation of a spectrographic components.

48. The computer-readable storage media of claim 33, wherein the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.

49. The computer-readable storage media of claim 34, further comprising:
  select, based on the aphasia classification, a subtype classifier from a plurality of subtype classifiers; and
  submit at least the aphasia classification to the subtype classifier in order to receive a subtype classification.

50. A system comprising:
  one or more computers and one or more storage devices on which are stored instructions that are operable, when executed by the one or more computers, to cause the one or more computers to perform operations comprising:
    receiving a recording of spontaneous speech from a subject;
    using a machine learning speech quantifying classifier to produce a speech quantifying score based at least in part on the spontaneous speech;
    generating comprehension feature values from the spontaneous speech;
    using a machine learning comprehension classifier to produce a comprehension score based at least in part on the comprehension feature values, the comprehension classifier trained using training comprehension feature values and corresponding training comprehension scores;
    determining an aphasia classification based on at least one of the speech quantifying score and the comprehension score; and
    using the aphasia classification to process at least one of the spontaneous speech and the subject.

51. The system of claim 50, further comprising:
generating speech quantifying feature values from the spontaneous speech and wherein using the machine learning speech quantifying classifier to produce the speech quantifying score based at least in part on the spontaneous speech comprises using the machine learning speech quantifying classifier to produce the speech quantifying score based at least in part on the speech quantifying feature values, the machine learning speech quantifying classifier trained using training speech quantifying feature values and corresponding training speech quantifying scores.

52. The system of claim 50, wherein using a machine learning comprehension classifier to produce a comprehension score based at least in part on the comprehension feature values comprises using a machine learning comprehension classifier to produce a comprehension score based at least in part on the comprehension feature values and on the speech quantifying score.

53. The system of claim 50, wherein the machine learning speech quantifying classifier is trained using training spontaneous speech and corresponding training speech quantifying scores.

54. The system of claim 50, wherein the determining an aphasia classification based on at least one of the speech quantifying score and the comprehension score further comprises submitting the speech quantifying score and the comprehension score to an aphasia classifier to receive an aphasia classification, the aphasia classifier trained using training speech quantifying scores and training comprehension scores and corresponding training aphasia classifications.

55. The system of claim 50, wherein determining an aphasia classification comprises determining a set of aphasia confidence values for different types of aphasia and then using those confidence values to select an aphasia classification.

56. The system of claim 50, wherein the system generates comprehension feature values from the spontaneous speech and submits the comprehension feature values to a comprehension classifier to produce a comprehension score only if the speech quantifying score exceeds a threshold.

57. The system of claim 50, wherein the recording comprises at least one of i) a video recording; ii) an audio recording, and iii) a text transcript.

58. The system of claim 50, further comprising:
  receiving an initial recording, wherein the initial recording comprises i) a video recording of the subject or ii) an audio recording of the subject; and
  generating a text transcript from the initial recording.

59. The system of claim 50, wherein the speech quantifying classifier is trained on a first training set that comprises recordings that have been tagged with corresponding training speech quantifying scores.

60. The system of claim 50, wherein the comprehension classifier is trained on a second training set that comprises training speech quantifying scores and a plurality of training feature values that have been tagged with corresponding training comprehension scores.

61. The system of claim 50, wherein the aphasia classifier is trained on a third training set that comprises training speech quantifying scores, training comprehension scores, and a plurality of training feature values that have been tagged with corresponding training aphasia classifications.

62. The system of claim 50, wherein the speech quantifying score is in units of words-per-specified time period.

63. The system of claim 51, wherein the speech quantifying feature values comprise one or more of:
  sounds per minute;
  words per minute;
  unique words per minute;
  a verb list;
  a count of a number of verbs;
  a proportion of valid words that are verbs;
  a noun list;
  a count of a number of nouns;
  a proportion of valid words that are nouns;
  a count of number of times a word was repeated twice in a row; and
  a representation of a spectrographic components.

64. The system of claim 50, wherein the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.

65. The system of claim 50, the system further comprising:
  selecting, based on the aphasia classification, a subtype classifier from a plurality of subtype classifiers; and
  submitting at least the aphasia classification to the subtype classifier in order to receive a subtype classification.

The invention claimed is:
1. A method comprising:
  receiving a tagged recording of spontaneous speech from a subject, wherein the tagged recording is associated with a tagged brain image;
  using a machine learning speech quantifying classifier to produce a tagged speech quantifying score based at least in part on the spontaneous speech;
  generating tagged comprehension feature values from the tagged recordings of spontaneous speech;
  using a machine learning comprehension classifier to produce a tagged comprehension score based at least in part on the tagged comprehension feature values, the comprehension classifier trained using training comprehension feature values and corresponding training comprehension scores;

determining an aphasia classification based on at least one of the tagged speech quantifying score and the tagged comprehension score;

tagging a brain image of a plurality of brain images with a corresponding aphasia tagging classification, to create a plurality of tagged brain images; and training, with the tagged brain images, a brain image aphasia classifier configured to i) receive brain images and ii) return an aphasia classification.

2. The method of claim 1, wherein the method further comprises:

generating tagged speech quantifying feature values from the spontaneous speech and wherein using the machine learning speech quantifying classifier to produce the tagged speech quantifying score based at least in part on the spontaneous speech comprises using the machine learning speech quantifying classifier to produce the tagged speech quantifying score based at least in part on the tagged speech quantifying feature values, the machine learning speech quantifying classifier trained using training tagged speech quantifying feature values and corresponding tagged training speech quantifying scores.

3. The method of claim 1, wherein using a machine learning comprehension classifier to produce a tagged comprehension score based at least in part on the tagged comprehension feature values comprises using a machine learning comprehension classifier to produce a tagged comprehension score based at least in part on the tagged comprehension feature values and on the tagged speech quantifying score.

4. The method of claim 1, wherein the machine learning speech quantifying classifier is trained using tagged training spontaneous speech and corresponding tagged training speech quantifying scores.

5. The method of claim 1, wherein the determining an aphasia classification based on at least one of the tagged speech quantifying score and the tagged comprehension score further comprises submitting the tagged speech quantifying score and the tagged comprehension score to an aphasia classifier to receive a tagged aphasia classification, the aphasia classifier trained using tagged training speech quantifying scores and tagged training comprehension scores and corresponding training aphasia classifications.

6. The method of claim 1, wherein determining an aphasia classification comprises determining a set of tagged aphasia confidence values for different types of aphasia and then using those tagged aphasia confidence values to select an aphasia classification.

7. The method of claim 1, wherein the method generates tagged comprehension feature values from the spontaneous speech and submits the tagged comprehension feature values to a comprehension classifier to produce a tagged comprehension score only if the tagged speech quantifying score exceeds a threshold.

8. The method of claim 1, the method further comprising:

receiving an initial recording, wherein the initial recording comprises i) a video recording of the subject or ii) an audio recording of the subject; and generating a text transcript from the initial recording.

9. The method of claim 2, wherein the tagged speech quantifying feature values comprise one or more of:

sounds per minute;
words per minute;
unique words per minute;
a verb list;
a count of a number of verbs;
a proportion of valid words that are verbs;
a noun list;
a count of a number of nouns;
a proportion of valid words that are nouns;
a count of number of times a word was repeated twice in a row; and
a representation of a spectrographic components.

10. The method of claim 1, wherein the plurality of possible aphasia types comprise Mixed Transcortical Aphasia, Broca's Aphasia, Transcortical Motor Aphasia, Wernicke's Aphasia, Transcortical Sensory Aphasia, Conduction Aphasia, Anomic Aphasia, Primary Progressive Aphasia, and a no-aphasia group.

11. The method of claim 1, further comprising:

receiving a brain image from a subject;

using the brain image classifier to produce an aphasia classification, wherein the brain image classifier is trained according to the method of claim 7.

* * * * *